(12) United States Patent
Rinaldi et al.

(10) Patent No.: US 9,089,156 B2
(45) Date of Patent: Jul. 28, 2015

(54) REDUCING MUSCLE SORENESS WITH GLUCOSAMINE COMPOSITIONS

(75) Inventors: Vincent Rinaldi, Valhalla, NY (US); William Racicot, Deer Park, IL (US); Jeffrey J. Zachwieja, Cary, IL (US); Robert Murray, Fox River Grove, IL (US)

(73) Assignee: Stokely-Van Camp, Inc., Chicago, IL (US)

( * ) Notice: Subject to any disclaimer, the term of this patent is extended or adjusted under 35 U.S.C. 154(b) by 1070 days.

(21) Appl. No.: 11/758,493

(22) Filed: Jun. 5, 2007

(65) Prior Publication Data
US 2007/0292483 A1   Dec. 20, 2007

Related U.S. Application Data

(60) Provisional application No. 60/811,306, filed on Jun. 5, 2006.

(51) Int. Cl.
| | |
|---|---|
| A23C 9/13 | (2006.01) |
| A23L 1/30 | (2006.01) |
| A23L 1/304 | (2006.01) |
| A23L 2/385 | (2006.01) |
| A23L 1/29 | (2006.01) |

(52) U.S. Cl.
CPC ............ *A23L 1/296* (2013.01); *A23C 9/1307* (2013.01); *A23L 1/30* (2013.01); *A23L 1/304* (2013.01); *A23L 2/385* (2013.01); *A23V 2002/00* (2013.01)

(58) Field of Classification Search
CPC ............ A61K 31/7008; A23V 2250/308; A23L 2/385; A23L 2/39; A23L 2/395; A23L 1/296; A23C 9/1307
See application file for complete search history.

(56) References Cited

U.S. PATENT DOCUMENTS

| | | | | |
|---|---|---|---|---|
| 4,766,209 | A | * | 8/1988 | Chen et al. .................... 536/55.3 |
| 6,482,456 | B1 | * | 11/2002 | Yokoo et al. ................. 426/330.3 |
| 6,632,804 | B2 | * | 10/2003 | Ekanayake ....................... 514/62 |
| 6,660,308 | B1 | | 12/2003 | Martin et al. |
| 2001/0051134 | A1 | | 12/2001 | Pandya |
| 2003/0069202 | A1 | * | 4/2003 | Kern et al. ........................ 514/46 |
| 2003/0104107 | A1 | * | 6/2003 | Gillota .............................. 426/590 |
| 2003/0124200 | A1 | * | 7/2003 | Stone ............................ 424/600 |
| 2003/0185904 | A1 | | 10/2003 | Reynolds |
| 2004/0071855 | A1 | * | 4/2004 | Wassenaar .................... 426/590 |
| 2004/0077055 | A1 | * | 4/2004 | Fosdick et al. ................. 435/85 |

FOREIGN PATENT DOCUMENTS

JP   2004-067562   3/2004

OTHER PUBLICATIONS

FDA Guidance for Industry on Container Closure Systems for Packaging Human Drugs and Biologics, May 1999.*
Definition of prevent, WordNet, http://wordnet.princeton.edu, accessed online Nov. 14, 2007.*
Entry for muscle pain, MayoClinic.com, http://mayoclinic.com/health/muscle-pain/MY00113/, accessed online Nov. 5, 2009.*
Definition of derivative, Oxford English Dictionary, http://dictionary.oed.com, accessed online on May 20, 2010.*
FDA Guidance for Industry: Notification of a Health Claim or Nutrient Content Claim Based on an Authoritative Statement of a Scientific Body, Jun. 11, 1998, http://www.fda.gov, accessed online on Dec. 27, 2012.*
Definitions of provide, Dictionary.com, http://dictionary.reference.com/browse/provide?s=t&path=/, accessed online on Jul. 22, 2013.*
Uzzan et al., Journal of Food Science, 2007, 72(3), p. E109-E114, first published online: Mar. 2, 2007.*
Ron W. Shaw, PhC MPS DBM, "Joint Food," Alternative Health Supplies (Australia), retrieved online at http://www.alternativehealth.com.au/Product/joint_food.htm, Oct. 29, 2007.

* cited by examiner

*Primary Examiner* — Jonathan S Lau
(74) *Attorney, Agent, or Firm* — Banner & Witcoff, Ltd.

(57) ABSTRACT

Edible compositions, such as sports drinks which limit muscle soreness, and methods of making and using the same are provided. Existing food products are commonly used during exercise to quickly replace fluids and electrolytes lost by sweating and/or to supply a boost of carbohydrates to improve sports or exercise performance. Aspects of the invention relate to compositions including glucosamine to alleviate or prevent muscle soreness. In certain embodiments, the glucosamine may be derived from a plurality of glucosamine sources. Further aspects relate to concentrated products for preparing beverage compositions. In certain embodiments, a concentrated form of a beverage composition may be provided in a packaging. Instructions for preparing the beverage composition having an effective amount of glucosamine may also be provided. Further embodiments may include a notification that indicates the benefit of reducing or preventing muscle soreness following physical exertion by consuming the beverage formulation.

5 Claims, No Drawings

REDUCING MUSCLE SORENESS WITH GLUCOSAMINE COMPOSITIONS

FIELD OF THE INVENTION

The present invention relates generally to edible compositions. More specifically, aspects of the invention relate to food and beverage products which limit muscle soreness and methods of making and using the same.

BACKGROUND OF THE INVENTION

Muscle soreness, or the feeling of muscle pain, is the normal response to unaccustomed exercise or exertion. It is usually experienced by people who have overworked their muscles. Muscle soreness can be caused by several factors, including small tears in muscle fiber or connective tissues, muscle spasms, or overstretching of the muscle. Commonly experienced as a loss of strength and decreased range of motion and neuromuscular function, muscle soreness can negatively affect sports performance and the enjoyment of exercise.

Various beverages categorized as sports drinks or energy drinks (collectively sports drinks) are commonly used during exercise to quickly replace fluids and electrolytes lost by sweating and/or to supply a boost of carbohydrates to improve sports or exercise performance. Such conventional sports drinks, however, fail to relieve or alleviate muscle soreness. Reducing or preventing muscle soreness would allow individuals to undertake increased levels of activity without undo discomfort. Allowing individuals to undertake increased levels of physical activity while experiencing limited or no muscle soreness would promote activity and healthier lifestyles. Further providing ready-made food or beverage products or concentrated formulations for limiting muscle soreness would promote users to consume an adequate amount of product to realize the benefit.

SUMMARY OF THE INVENTION

Aspects of the invention relate to a food or beverage composition. The composition may be provided in various physical forms. For example, a composition may be provided in dry, gel or concentrated liquid form, which may be mixed with one or more liquids for drinking or for drinking with a liquid. Alternatively, a beverage composition may be provided as a ready-to-drink beverage. In one embodiment, the beverage composition includes glucosamine to limit muscle soreness. In certain embodiments, the glucosamine may be derived from a plurality of glucosamine sources.

In certain beverage-related embodiments, the effective amount of glucosamine provided to limit muscle soreness is about 2 milligrams to about 10 milligrams per milliliter of the beverage composition. Select beverage compositions, such as sports drinks, may further comprise one or more electrolytes, such as for example, potassium, magnesium, calcium, and chloride. Other embodiments of the beverage composition may be formulated as, for example, a shake, a smoothie, or a diet drink. Still further embodiments of beverage formulations may provide an indication to a consumer to consume at least about 1,500 mg of glucosamine for at least one day to limit muscle soreness.

Further aspects relate to concentrated products for preparing beverage compositions. In certain embodiments, a concentrated form of a beverage composition may be provided in a packaging. The concentrated beverage composition may be in any physical form, such as for example, a powder, a gel, a solid, a liquid, and combinations thereof. Instructions for preparing the beverage composition may also be provided, such that when the instructions are followed, they provide a beverage composition having an effective amount of glucosamine. Further embodiments may include a notification that indicates the benefit of reducing or preventing muscle soreness following physical exertion that can be realized by consuming the beverage formulation.

Additional embodiments relate to reducing muscle soreness with glucosamine-containing compositions in combination with other foods. Further additional embodiments relate to methods of doing business relating to providing compositions for reducing muscle soreness, where the compositions contain glucosamine and/or related substances.

DETAILED DESCRIPTION

Aspects of the invention relate to beverage compositions. The beverage composition includes an enhancer for limiting muscle soreness. As used herein, the terms limit and limiting refer to the reduction of muscle soreness. In some embodiments, muscle soreness may be substantially reduced to a level where it may be considered non-existent. In further embodiments, ingestion of the beverage may limit the onset of all or a portion of any subsequent muscle soreness, thus providing a preventative quality.

Other ingredients, such as flavoring agents, coloring agents, or other ingredients may also be included, as described in more detail below. The enhancer, in one embodiment, comprises at least one glucosamine source. Various types of glucosamine sources may be used to incorporate glucosamine into the beverage composition. The glucosamine source may include, for example, glucosamine compounds such as glucosamine hydrochloride, glucosamine sulfate, glucosamine iodide, glucosamine chlorohydrate, N-acetyl glucosamine, or a combination thereof. Other glucosamine sources, such as salts and derivatives of glucosamine, or substituted glucosamine, are also within the scope of this disclosure. In one embodiment, a glucosamine source that is generally regarded as non-allergenic is formulated into the beverage. In one specific embodiment, at least one glucosamine source comprises glucosamine hydrochloride (HCl). In such an embodiment, the inventors have discovered that REGENASURE, commercially available from Cargill Health and Food Technologies, Minneapolis, Minn. provides suitable results. Other sources of glucosamine are commercially available from: Watson Inc., West Haven, Conn.; Alfa Chem Corp., Rio Piedras, P R; P.L. Thomas & Co., Inc., Morristown, N.J.; NutriScience Innovations, LLC., Fairfield, Conn.; Functional Foods Corp., Englishtown, N.J. and Buckton Scott Nutrition Inc, Fairfield, N.J. As will be appreciated by those skilled in the art upon review of this disclosure, one or more glucosamine-containing products may serve as a glucosamine source. Selection of one or more glucosamine sources may depend on a myriad of factors, such as, for example, cost, production quantity, solubility, stability, shelf life, and consumer preference. Hyaluronic acid and related compounds are also encompassed by this invention, and may be used in conjunction with another glucosamine source or independently, and is within the scope of this disclosure as a glucosamine source.

Exemplary embodiments of beverage compositions comprising a measurable quantity of glucosamine hydrochloride as the illustrative glucosamine source are provided below. As will be readily appreciated by those skilled in the art upon review of the following, the amount of glucosamine hydrochloride (or other source of glucosamine) present among different embodiments will depend on a myriad of factors, including but not limited to: the targeted amount of glucosamine to deliver to the consumer, information regarding targeted consumers, the type of beverage composition (i.e., a sports drink, a diet beverage, a smoothie or a shake), special considerations for packaging and shipping, and/or specific ingredients in the composition.

In select embodiments, it may be desirable to deliver about 500-1,500 mg of glucosamine to a consumer. The targeted range of glucosamine may depend on a myriad of factors, such as for example, metabolism, body chemistry and/or the amount of physical activity. For example, a beverage composition formulated for a professional athlete undergoing strenuous physical exertion in a hot, arid environment may comprise a different ratio of glucosamine hydrochloride than a beverage composition formulated for a recreational consumer who undergoes light exercise in a more tepid environment. Using the two potential consumers as an example, the professional athlete may likely ingest several dozen ounces of the beverage composition during a single training session or event, therefore the amount of glucosamine per unit of the overall beverage composition may be relatively low, such as below 1 mg/ml. Thus, a 64 ounce sports drink having about 0.8 mg of glucosamine hydrochloride per milliliter of the beverage composition may provide the targeted amount of glucosamine to the professional athlete while also providing a large quantity of fluids to compensate for heavy perspiration. As described later in this disclosure, the sports drink may further comprise electrolytes or other ingredients to provide further benefits.

In many scenarios, recreational consumers will consume far less fluids during and subsequently after exercise than the professional athlete. Thus, beverage compositions targeted towards the recreational consumer may be formulated with a higher ratio of glucosamine per milliliter to deliver about the same amount of glucosamine in less volume. In one embodiment, the beverage is formulated to deliver around about 8 to about 10 mg of glucosamine hydrochloride per milliliter (other factors, described below may contribute to the amount delivered to the consumer, and thus may increase or decrease the amount of glucosamine source provided in the beverage). The beverage composition for the professional athlete, the recreational consumer, or any intended consumer, may be prepared from a concentrate. Therefore, select embodiments of beverage formulations or concentrates for preparing beverage compositions may comprise instructions for preparing and/or consuming the beverage composition in a manner that provides the consumer with a targeted amount of glucosamine.

In one embodiment, beverage compositions (provided as is or when made from concentrate) provide at least about 500 to about 1,500 mg of glucosamine for a daily regimen. In one such embodiment, 1500 mg per day of glucosamine may be ingested through several servings of the glucosamine-containing products, such as the beverage compositions. Yet, in some embodiments the provided beverage composition may supply a full targeted amount of glucosamine for a daily regimen. This may be especially advantageous to ensure consumers receive a consistent minimum daily intake of glucosamine as the inventors believe the effectiveness of glucosamine in reducing muscle soreness may be increased with a regular daily regimen of consuming the dosage amounts describe herein. As discussed above, some consumers may undertake less physical exertion than others, thus less glucosamine may be provided to limit any subsequent muscle soreness. This may be ideal for example when elevated levels may provide any off taste flavors or the like. Further, the inventors have also realized that amounts greater than about 1500 mg may also be useful.

Special considerations in packaging, shipping, and or formulations may also be considered when delivering a targeted amount of glucosamine in the beverage compositions. As an example, shake-type beverages, such as the beverage composition provided in Table 3, are generally formulated to have a relatively neutral pH value. Glucosamine hydrochloride degrades at a quickened rate when formulated in beverages having neutral pHs, therefore, the glucosamine may be provided at a higher ratio than the intended to be ingested by the consumer.

In one embodiment, beverage compositions exhibiting a relatively neutral pH may be formulated to have around about 20 mg/ml of glucosamine to compensate for degradation of the glucosamine. Such a formulation was determined to deliver 1,500 mg of glucosamine based on results from a storage study. During the study, in which such beverages were stored for a period of 12 months at ambient (73 degrees Fahrenheit) temperature, it was determined that approximately 77% of glucosamine originally present had degraded during a 12 month storage period. Thus, information regarding the average shelf-life and/or delivery mechanisms for specific products may be utilized when formulating the beverage compositions. Such factors may include the temperature, time to consumption, packaging the compositions are stored within, among others.

In certain embodiments, a beverage composition comprises about 0.1954 to 0.9272 wt % of glucosamine HCl. In yet another embodiment, the effective amount of glucosamine HCl is about 0.1954—about 0.4886 wt %, about 0.3709—about 0.9272 wt % or about 0.1954—about 0.2931 wt % of the beverage composition. Further embodiments of beverage compositions may encompass products containing hyaluronic acids, and similar compounds, in addition to or in lieu of glucosamine hydrochloride.

As shown in the exemplary beverage compositions in Tables 1-3, other ingredients may be present in the beverage composition, such as electrolyte sources, flavoring, coloring, and carbohydrate sources. In one embodiment, an isotonic beverage comprising electrolytes is provided. Providing one or more electrolytes aids in, for example, fluid absorption in the small intestines and helps to maintain osmotic balance in the body. Isotonic beverages are particularly useful for rehydrating the body during, for example, heightened physical activities.

In one embodiment, the beverage composition includes an electrolyte source for providing sodium (Na). Sodium may be provided by compounds of sodium, such as sodium chloride, sodium citrate, sodium carbonate, sodium bicarbonate, or combinations thereof. In select embodiments, the amount of sodium is about 0.03—about 0.06 wt % of the beverage. Other amounts may also be useful, depending on the application and other factors. In one embodiment, the sodium is provided by sodium chloride and sodium citrate. As shown in both exemplary formulations in Table 1 and Table 2, the sodium citrate is about 0.0659% wt of the beverage composition and sodium chloride is about 0.0659 wt % of the beverage composition.

Additional types of electrolyte sources to provide, for example, potassium (K), magnesium (Mg), calcium (Ca) and chloride (Cl) ions can also be included in the beverage composition in addition to or independently of sodium (Na). The different types of electrolytes can be provided by their compounds or a combination of their compounds. For example, the compounds can include potassium acetate, potassium bicarbonate, potassium bromide, potassium chloride, potassium citrate, potassium-D-gluconate, mono- and dibasic potassium phosphate, calcium acetate, calcium chloride, calcium citrate, calcium-D-gluconate, calcium lactate, calcium laevulinate, dibasic calcium phosphate, magnesium chloride, magnesium carbonate and magnesium sulphate, or a combination thereof. In one embodiment, the potassium ions are provided by monopotassium phosphate or dipotassium phosphate. In one such embodiment, monopotassium phosphate comprises around about 0.0439 wt % of the beverage composition. In another embodiment, the beverage may contain about 0.01—about 0.04 wt % of potassium, about 0.01—about 0.02 wt % of magnesium, about 0.001—about 0.003 wt % of calcium, about 0.02—about 0.03 wt % of chloride. Other amounts or combinations may also be useful.

Beverage compositions according to different embodiments may comprise one or more carbohydrate source(s). Carbohydrates may provide energy to the muscles, improving endurance performance. The carbohydrate source comprises, for example, aldohexoses, monosaccharides, disaccharides and polysaccharides, or a combination thereof. Such sugars include glucose, glucose polymers, maltose, maltodextrins, maltotriose, lactose, galactose, sucrose, high fructose corn syrup (HFCS), and sucanat ketohexoses, such sugars being arabinose, ribose, fructose, sorbose, tagatose and sorbitol.

The carbohydrate source may comprise complex carbohydrates, simple sugars, and combinations thereof. For example, the carbohydrate source(s) may comprise both sucrose and HFCS. In one embodiment, the total amount of carbohydrate source is about 6% by weight, however, carbohydrates need not be included in the formulations. Carbohydrate content can vary generally from about 4% to about 10% for a beverage product, but this range can be extended for other products, such as sports bars and other food products containing glucosamine to limit muscle soreness. Based on the guidance provided herein, formulating such other products will be well within the ability of one skilled in the art of formulating food products; such products are also covered by the scope of this invention.

Non-mineral nutritive compounds such as vitamins can be added to the beverage composition. Vitamins such as Vitamin A, Vitamin B, Vitamin C, Vitamin D and Vitamin E may be provided in various embodiments. The beverage composition can also include a pH adjuster, for example, citric acid. Other types of pH adjusters or a combination of pH adjusters may also be present in various embodiments prepared in accordance with the invention. The pH of certain beverage compositions may be formulated to be generally at about 2.0 to about 4.0. Such pH levels may be desirable for a variety of formulations, such as for example, a "non-shake" type beverage. Non-limiting formulations of exemplary "non-shake" type beverages are described in Table 1 and Table 2 below. The pH range for a "shake" type beverage (for example, such as one containing milk-based ingredients such as milk protein) according to select embodiments, may generally have a higher pH. As one exemplary formulation, the pH of the "shake" type beverage exemplified in Table 3 below may be formulated to be generally in the range of about 6.0 to about 8.0.

Additional ingredients that are recommended for use in a beverage (or non-beverage) formulation for reducing muscle soreness, according to the teaching of this invention, include tart fruit juices, such as cherry juice. Non-limiting additional examples of other useful juices include natural juices such as orange juice, grape juice, pineapple juice, lemon juice and lime juice. The percentage of juice may vary, and several different juices may be added to a formulation. According to certain embodiments, a portion or all of the water in a formulation may be replaced with fruit juice. In non-beverage embodiments, powdered juices or juice concentrates can be added. Some alteration of acidic ingredients in a formulation may be recommended for sensory purposes when fruit juices are used, but such alterations are be within the skill of a person with experience as a formulator.

In embodiments providing a packaged ready-to-drink beverage, the beverage composition may be pre-mixed with a liquid such as water. Other types of liquids are may also be incorporated or replace the water as discussed above. In certain embodiments, the ready-to-drink beverage comprises about 80-99 weight percent (wt %) of liquid of the total weight of the beverage. Unless otherwise specified, all weight percentages are based on the total weight of a ready-to-drink beverage. In further embodiments, the beverage composition can be packaged as an edible composition or concentrate, such as a dry mix (e.g., powder) or a liquid concentrate for later reconstitution with one or more liquids to form a beverage. The concentrated composition may be associated with instructions for preparing the beverage composition that when followed provide the beverage composition having an effective amount of glucosamine to limit muscle soreness following physical exertion. Further embodiments may include a notification that indicates the benefit of limiting muscle soreness following physical exertion that can be realized by consuming the beverage formulation.

In another embodiment, a beverage concentrate may be packaged as gels, capsules, or tablets which are consumed with liquid. When provided in these forms, the beverage composition may comprise instructions to mix or consume with an amount of liquid which is equal to about 80-99 wt % of the prepared beverage composition. In additional embodiments, the reduction in muscle soreness may be achieved with non-beverage forms of food products, such as "sports" bars containing appropriate levels of glucosamine per serving size. Again, a skilled formulator could design alternate, non-beverage product forms, and add the appropriate amount of glucosamine additive to result in effective alleviation or prevention of muscle soreness.

Additionally, non-beverage type products can be formulated based on the guidance given herein and are within the scope of this disclosure. Such other product forms may include, but are not limited to, sports or performance bars, sports or performance gels, chewing gum, sublingual strips, gummy-based products, and confectionery type products. These are merely exemplary of other product forms that can be designed for reducing or avoiding muscle soreness based on the teachings herein. Other product forms will be within the skill of a product formulator when considered together with the teachings provided herein.

Further embodiments relate to products and methods of reducing or alleviating muscle soreness comprising providing a glucosamine-containing composition together with one or more edible compositions. Such other compositions can be chosen based on known or suspected ability to promote health, performance, body healing or recovery, or for other reasons such as consumer or marketing appeal. Specific embodiments include pre-packaged food products comprising a glucosamine containing composition and one or more other food items. The composition of the glucosamine-containing item can vary greatly, depending on how it is to be consumed with the other food item or items. For example, if the other food item is a fruit juice, the glucosamine-containing composition may be formulated with less flavor, acid, or water, for example. Other non-limiting examples include combining a liquid glucosamine-containing composition with a powdered or syrup-like food item. An additional non-limiting embodiment is one in which the glucosamine-containing composition and other food item are both powders. Also, embodiments are covered where in addition to the glucosamine-containing composition and other food item, other devices are added to the package to complement or add additional value to the final product. For example, mixing utensils may be added to the overall package, condiments may be added, a cup or other vessel may be added to the package. A non-limiting example of a glucosamine-containing composition and food item in combination with an additional device is one in which a cup and/or spoon is packaged together with a powdered food item and/or a powdered form of a glucosamine-containing composition. The product can be designed to be mixed together with further addition of a liquid, such as water. The product may be light and convenient to carry, and usable where water is available. The above embodiments are non-limiting, and other useful combination products for reducing or alleviating muscle soreness are encompassed by this invention.

Further additional embodiments of this invention include methods of doing business by providing and/or promoting consumption of a glucosamine-containing composition to limit muscle soreness. The discovery and promotion of key health-related benefits of food compositions provides important contributions to society. This invention teaches embodiments with important benefits to limit muscle soreness. Therefore, additional embodiments include a variety of products, packaged combinations of products, and promotion in general, for reducing and/or avoiding muscle soreness with glucosamine-containing compositions.

EXEMPLARY EMBODIMENTS

Various examples of beverage composition are provided in following tables.

TABLE 1

Isotonic Drink with Carbohydrate
(0 g total fat, 14 g total carbohydrate, 0-1 g
total protein per 240 ml serving)

| Ingredients | % Batch |
|---|---|
| Water | 90.4536-90.8148 |
| HFCS (42%) | 4.2876 |
| Liquid Sucrose | 4.2155 |
| Sodium Chloride | 0.0659 |
| Sodium Citrate | 0.0659 |
| Monopotassium Phosphate | 0.0439 |
| Glucosamine HCL (Cargill, Minneapolis, MN) | 0.1954-0.4886 |
| Citric Acid | 0.2700 |
| Flavor | 0.0370-0.0950 |
| Ester Gum (Glycerol ester of wood rosin) | 0.0020-0.0060 |
| FDC Color | 0.0010-0.0060 |
| Vegetable Oil | 0.0010-0.0020 |
| Total | 100.00 |

TABLE 2

Isotonic Drink without Carbohydrate
(0 g total fat, 0 g total carbohydrate, 0-1 g
total protein per 240 ml serving)

| Ingredients | % Batch |
|---|---|
| Water | 99.3158-98.9546 |
| Sodium Chloride | 0.0659 |
| Sodium Citrate | 0.0659 |

TABLE 2-continued

Isotonic Drink without Carbohydrate
(0 g total fat, 0 g total carbohydrate, 0-1 g
total protein per 240 ml serving)

| Ingredients | % Batch |
|---|---|
| Monopotassium Phosphate | 0.0439 |
| Citric Acid | 0.2457 |
| Glucosamine HCL (Cargill, Minneapolis, MN) | 0.1954-0.4886 |
| Acesulfame Potassium | 0.0072 |
| Sucralose Liquid (25% solution) | 0.0192 |
| Flavor | 0.0370-0.0950 |
| Ester Gum (glycerol ester of wood rosin) | 0.0020-0.0060 |
| FDC Color | 0.0010-0.0060 |
| Vegetable Oil | 0.0010-0.0020 |
| Total | 100.00 |

TABLE 3

Isotonic Shake
(1.5 g total fat, 40 g total carbohydrate, 20 g total
protein per 325 ml serving)

| Ingredients | % Batch |
|---|---|
| Water | 80.0403-80.5966 |
| Dry Sugar | 10.2600 |
| Dipotassium Phosphate | 0.3000 |
| Salt | 0.1500 |
| Chocolate Flavor | 0.2000 |
| Glucosamine HCL (Cargill, Minneapolis, MN) | 0.3709-0.9272 |
| Mono & Di-glyceride beads (derived from esterified glycerol & triglyceride) | 0.2500 |
| Avicel CL-611 (FMC Corp., Philadelphia, PA) | 0.5000 |
| Carrageenan | 0.0300 |
| Antifoam (polydimethyl siloxane) | 0.0075 |
| Milk Protein Isolate (Ultranor Milk Protein Isolate-9060 from Kerry) | 6.4350 |
| Cocoa Powder | 0.9000 |
| Total | 100.00 |

What is claimed is:

1. A shake beverage product comprising: a glucosamine source consisting of glucosamine HCl, that when consumed provides about 500-1500 mg of glucosamine limit muscle soreness following physical exertion; at least one electrolyte source providing an electrolyte selected from the group consisting of sodium, chloride, potassium, calcium, magnesium and combinations thereof; at least one carbohydrate source; at least one milk-based ingredient; and having a pH of about 6.0 to about 8.0.

2. The product of claim 1, wherein the at least one electrolyte source comprises at least one selected from the group consisting of sodium chloride, sodium citrate, sodium carbonate, sodium bicarbonate, potassium chloride, calcium chloride, magnesium chloride, and combinations thereof.

3. The product of claim 2, wherein the at least one electrolyte source further comprises at least one selected from the group consisting of potassium acetate, potassium bicarbonate, potassium bromide, potassium chloride, potassium citrate, potassium-D-gluconate, monobasic potassium phosphate, dibasic potassium phosphate, calcium acetate, calcium citrate, calcium-D-gluconate, calcium lactate, calcium laevulinate, dibasic calcium phosphate, magnesium carbonate, magnesium sulphate, and combinations thereof.

4. The product of claim 1 wherein the at least one milk-based ingredient comprises milk protein.

5. The product of claim 4 wherein the milk protein comprises milk protein isolate.

\* \* \* \* \*